(12) United States Patent
Verbeke et al.

(10) Patent No.: US 11,385,884 B2
(45) Date of Patent: Jul. 12, 2022

(54) ASSESSING COGNITIVE REACTION TO OVER-THE-AIR UPDATES

(71) Applicant: HARMAN INTERNATIONAL INDUSTRIES, INCORPORATED, Stamford, CT (US)

(72) Inventors: Joseph Verbeke, San Francisco, CA (US); Joshua Sweers, Lansing, MI (US); Stefan Marti, Oakland, CA (US)

(73) Assignee: Harman International Industries, Incorporated, Stamford, CT (US)

( * ) Notice: Subject to any disclaimer, the term of this patent is extended or adjusted under 35 U.S.C. 154(b) by 0 days.

(21) Appl. No.: 16/398,163

(22) Filed: Apr. 29, 2019

(65) Prior Publication Data

US 2020/0341745 A1 Oct. 29, 2020

(51) Int. Cl.
| | |
|---|---|
| *G06F 9/44* | (2018.01) |
| *G06F 9/455* | (2018.01) |
| *G06F 9/445* | (2018.01) |
| *G06F 8/65* | (2018.01) |
| *G06F 17/15* | (2006.01) |
| *G06V 40/20* | (2022.01) |

(52) U.S. Cl.
CPC ............... *G06F 8/65* (2013.01); *G06F 17/15* (2013.01); *G06V 40/20* (2022.01)

(58) Field of Classification Search
CPC ....... G06F 8/65; G06F 17/15; G06K 9/00335; G06V 40/20
See application file for complete search history.

(56) References Cited

U.S. PATENT DOCUMENTS

| | | | |
|---|---|---|---|
| 10,157,423 B1 * | 12/2018 | Fields | B60W 50/0205 |
| 10,558,740 B1 * | 2/2020 | O'Malley | G06F 40/197 |
| 2003/0046401 A1 * | 3/2003 | Abbott | G06F 9/451 |
| | | | 709/228 |
| 2008/0091515 A1 | 4/2008 | Thieberger et al. | |
| 2013/0006395 A1 * | 1/2013 | Plache | G06F 3/04842 |
| | | | 700/83 |
| 2013/0121591 A1 * | 5/2013 | Hill | G10L 15/1815 |
| | | | 382/195 |
| 2013/0159228 A1 | 6/2013 | Meijer et al. | |

(Continued)

FOREIGN PATENT DOCUMENTS

| | | | | |
|---|---|---|---|---|
| DE | 102015200775 A1 * | 7/2016 | | G08B 21/06 |
| WO | WO-2019028376 A1 * | 2/2019 | | A61B 5/165 |

OTHER PUBLICATIONS

Mishel Johns, Effect of cognitive load in autonomous vehicles on driver performance, 2014, pp. 1-4. https://dl.acm.org/doi/pdf/10.1145/2667239.2667296 (Year: 2014).*

(Continued)

*Primary Examiner* — Mongbao Nguyen
(74) *Attorney, Agent, or Firm* — Artegis Law Group, LLP

(57) ABSTRACT

Techniques for determining a cognitive reaction to a software application update include determining that a software application executing on a computing device has been modified into an updated software application; acquiring, via at least one sensor, sensor data associated with a user of the updated software and determining, based on the sensor data, at least one of a cognitive workload and an emotional state associated with a user interaction with a feature of the updated software application.

20 Claims, 9 Drawing Sheets

(56) References Cited

U.S. PATENT DOCUMENTS

| | | | | |
|---|---|---|---|---|
| 2014/0003737 | A1* | 1/2014 | Fedorovskaya | G06Q 50/01 382/276 |
| 2015/0381938 | A1* | 12/2015 | Cunico | H04N 7/157 348/14.1 |
| 2016/0378965 | A1* | 12/2016 | Choe | A61B 5/332 726/19 |
| 2017/0039045 | A1* | 2/2017 | Abrahami | A61B 5/0205 |
| 2017/0160813 | A1* | 6/2017 | Divakaran | G10L 15/1815 |
| 2017/0249438 | A1* | 8/2017 | Jain | G16H 20/70 |
| 2018/0197150 | A1* | 7/2018 | Bender | G06Q 10/1095 |
| 2018/0307661 | A1* | 10/2018 | McDuff | G06T 11/60 |
| 2018/0314980 | A1* | 11/2018 | Osotio | G06F 3/048 |
| 2019/0028556 | A1* | 1/2019 | Ben-Harrush | H04L 67/306 |
| 2019/0049968 | A1* | 2/2019 | Dean | A61G 5/04 |
| 2019/0073618 | A1* | 3/2019 | Kanukurthy | G06Q 10/0635 |
| 2019/0188650 | A1* | 6/2019 | Humble | G06K 9/00335 |
| 2019/0239795 | A1* | 8/2019 | Kotake | G16H 50/30 |
| 2019/0274632 | A1* | 9/2019 | Kochura | A61B 5/7275 |
| 2019/0325240 | A1* | 10/2019 | Woo | G06K 9/00355 |
| 2020/0028810 | A1* | 1/2020 | Werner | G06K 9/00302 |
| 2020/0050936 | A1* | 2/2020 | Edelsten | G06F 8/30 |
| 2020/0074058 | A1* | 3/2020 | Son | G06N 3/0454 |
| 2020/0090394 | A1* | 3/2020 | Hong | G06F 17/18 |
| 2020/0150949 | A1* | 5/2020 | Jewkes | G06F 8/77 |
| 2020/0193239 | A1* | 6/2020 | Wilson | G06F 16/38 |
| 2020/0206631 | A1* | 7/2020 | Sumant | A63F 13/215 |
| 2020/0220933 | A1* | 7/2020 | Kwatra | H04L 67/125 |
| 2020/0253527 | A1* | 8/2020 | Ellison | A61B 5/165 |
| 2020/0272529 | A1* | 8/2020 | Suzuki | B60R 16/023 |
| 2020/0380882 | A1* | 12/2020 | Alailima | G09B 19/00 |

OTHER PUBLICATIONS

Vijay Govindarajan, Affective Driver State Monitoring for Personalized, Adaptive ADAS, 2018, pp. 1017-1022. https://ieeexplore.ieee.org/stamp/stamp.jsp?tp=&arnumber=8569585&isnumber=8569013 (Year: 2018).*

Min Chen, AIWAC: Affective Interaction Through Wearable Computing and Cloud Technology, 2015, pp. 20-27. https://ieeexplore.ieee.org/stamp/stamp.jsp?tp=&arnumber=7054715 (Year: 2015).*

Luca Longo, Experienced mental workload, perception of usability, their interaction and impacton task performance, 2018, pp. 1-36. https://journals.plos.org/plosone/article?id=10.1371/journal.pone.0199661 (Year: 2018).*

Novak et al, "Assessment of cognitive load through biometric monitoring", In Proceedings of the 7th International Conference on Information Society and Technology (ICIST 2017), vol. 1, 2017, pp. 303-306. http://www.eventiotic.com/eventiotic/library/paper/320.

Zarjam et al., "Spectral EEG features for evaluating cognitive load," 2011 Annual International Conference of the IEEE Engineering in Medicine and Biology Society, 2011, pp. 3841-3844. https://ieeexplore.ieee.org/document/6090954.

Le et al, "Investigation of spectral centroid features for cognitive load classification", Speech Communication 53, 4, (2011), pp. 540-551. DOI:https://doi.org/10.1016/j.specom.2011.01.005.

Extended European Search Report for application No. 20172152.9 dated Sep. 28, 2020.

Kolakowska et al., "Emotion Recognition and its Application in Software Engineering", 2013 6th International Conference on Human System Interactions (HSI), IEEE, XP032475640, ISSN: 2158-2246, DOI: 10.1109/HSI.2013.6577877, ISBN: 978-1-4673-5635-0, Jun. 6-8, 2013, pp. 532-539.

Munim et al., "Towards Developing a Tool for UX Evaluation Using Facial Expression", 2017 3rd International Conference On Electrical Information and Communication Technology (EICT), IEEE, XP033308192, DOI: 10.1109/EICT.2017.8275227, ISBN: 978-1-5386-2305-3, Dec. 7, 2017, pp. 1-6.

* cited by examiner

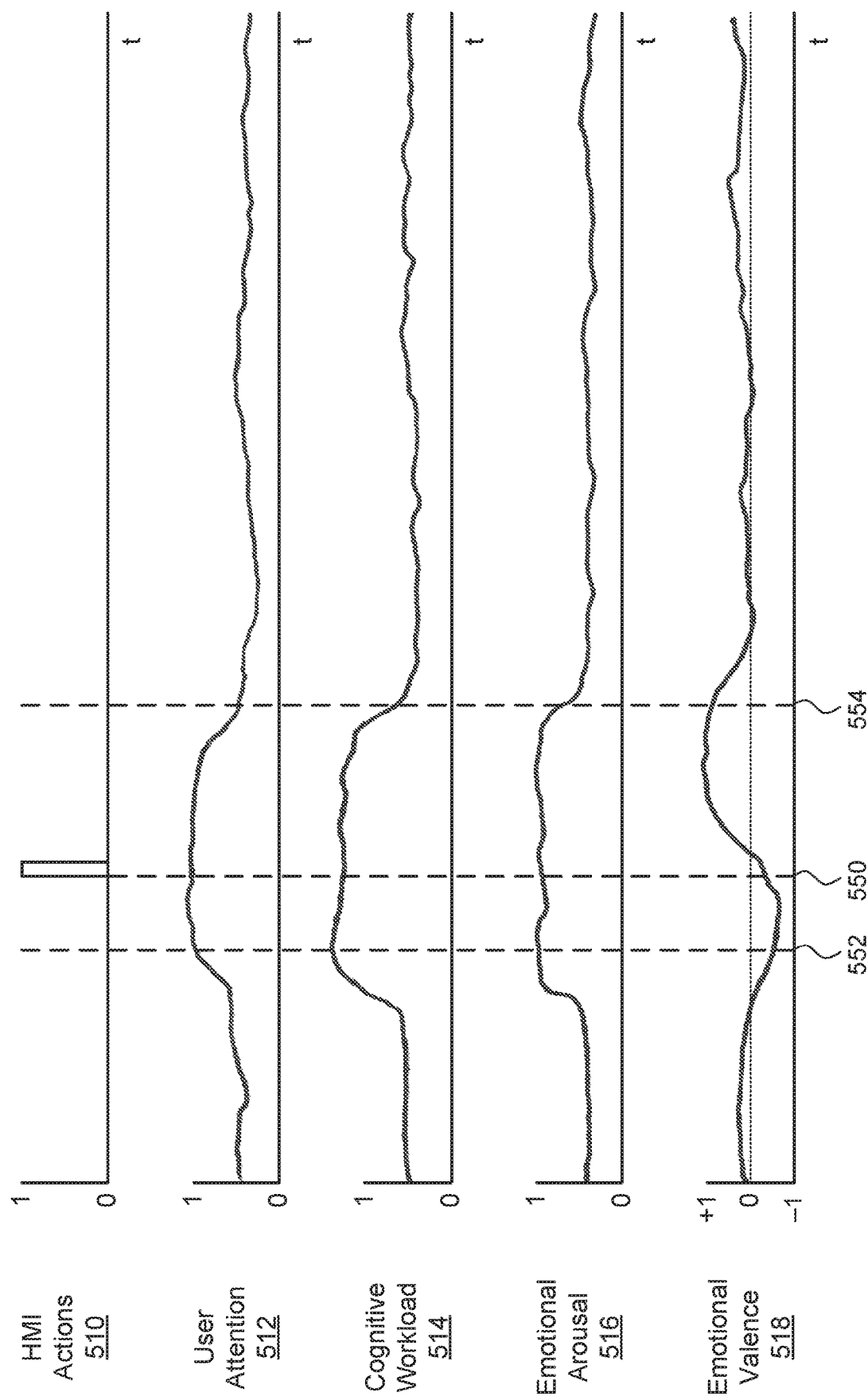

ASSESSING COGNITIVE REACTION TO OVER-THE-AIR UPDATES

BACKGROUND

Field of the Embodiments of the Present Disclosure

Embodiments of the present disclosure relate generally to psychophysiological sensing systems and, more specifically, to assessing cognitive reaction to over-the-air updates.

Description of the Related Art

Success of software applications often depends on the ease-of-use and intuitiveness of the human-machine interface (HMI). Over time, updates to a particular software application may add, delete, or modify certain features, typically necessitating a corresponding change in the HMI. Prior to releasing such an update to a software application, the software development team may perform user testing and/or quality assurance testing in a controlled environment. Such testing typically includes monitoring and conversing with a small set of users as they operate the HMI associated with the updated software application. This testing may be helpful to determine if the HMI associated with the updated software application is better, the same as, or worse than the HMI for the previous software application.

After completion of user testing, the software development team may change one or more elements of the HMI based on the user testing. The software development team then generates a new update and repeats the user testing to test the new update. After one or more iterations of generating a new update and performing testing on the new update, the software development team determines that the HMI for the new update is ready for general release. Then, the software development team releases the update to all users.

One problem with the above approach is that testing user reaction to an HMI for a new update is difficult once the update is released to the general user community. The software development team may gather feedback about a released update by performing an online survey for the update. Additionally, the software development team may request that a subset of users complete a written or oral survey regarding the update. The software development team may also gather feedback by reading online forums where users exchange information and reactions regarding the particular software application. By conducting surveys and reading user forums, the software development team may learn useful information that helps to inform changes to implement for the subsequent update to the software application.

One potential drawback to gathering feedback via user surveys and user forums is that surveys and forums are subject to various forms of bias. One such bias is that only users that have a particularly bad or a particularly good experience with an update to a software application may cooperate in a user survey or post to a user forum. Little to no feedback may be received from those users who have had a more-or-less neutral experience with the update, and this group of users may represent the largest quantity of user of the software application. As a result, the software development team may modify the software application based on feedback received from users on the extreme positive or negative ends of the user spectrum rather than on the majority of users. Further, there may be a significant delay between when the user first experiences the updated software application and when the user completes a survey or posts on a user forum. As a result, the information from customer surveys and forum posts may not accurately reflect the user experience as of the time the user was actually interacting with the updated software application, due to the fading of memory over time.

As the foregoing illustrates, improved techniques for determining user reactions to over-the-air updates would be useful.

SUMMARY

Various embodiments of the present disclosure set forth a computer-implemented method for determining a cognitive reaction to a software application update. The method includes determining that a software application executing on a computing device has been modified into an updated software application. The method further includes acquiring, via at least one sensor, sensor data associated with a user of the updated software application. The method further includes determining, based on the sensor data, at least one of a cognitive workload and an emotional state associated with a user interaction with a feature of the updated software application.

Other embodiments include, without limitation, an audio processing system that implements one or more aspects of the disclosed techniques, and a computer readable medium including instructions for performing one or more aspects of the disclosed techniques, as well as a method for performing one or more aspects of the disclosed techniques.

At least one technical advantage of the disclosed techniques relative to the prior art is that data associated with a user reaction to a software application update is acquired and analyzed after the update is released to users. As a result, user reaction to a new update may be continually assessed in the user environment after the update is released. Another technical advantage of the disclosed techniques is that, because the user reaction data is based on visual and/or psychophysiological information related to the user, the user reaction data is more accurate and less subject to bias relative to prior approaches, such as approaches involving user surveys and forum posts. As a result, a software development team is able to improve aspects of a software application based on a more accurate model of user reaction to a particular release of the software application. These technical advantages represent one or more technological improvements over prior art approaches.

BRIEF DESCRIPTION OF THE SEVERAL VIEWS OF THE DRAWINGS

So that the manner in which the recited features of the one or more embodiments set forth above can be understood in detail, a more particular description of the one or more embodiments, briefly summarized above, may be had by reference to certain specific embodiments, some of which are illustrated in the appended drawings. It is to be noted, however, that the appended drawings illustrate only typical embodiments and are therefore not to be considered limiting of its scope in any manner, for the scope of the disclosure subsumes other embodiments as well.

FIGS. 5A-5B illustrate example waveforms that illustrate cognitive workload and emotional state for a user associated with the system of FIG. 1, according to various embodiments.

DETAILED DESCRIPTION

In the following description, numerous specific details are set forth to provide a more thorough understanding of certain specific embodiments. However, it will be apparent to one of skill in the art that other embodiments may be practiced without one or more of these specific details or with additional specific details.

System Overview

Figure 1:
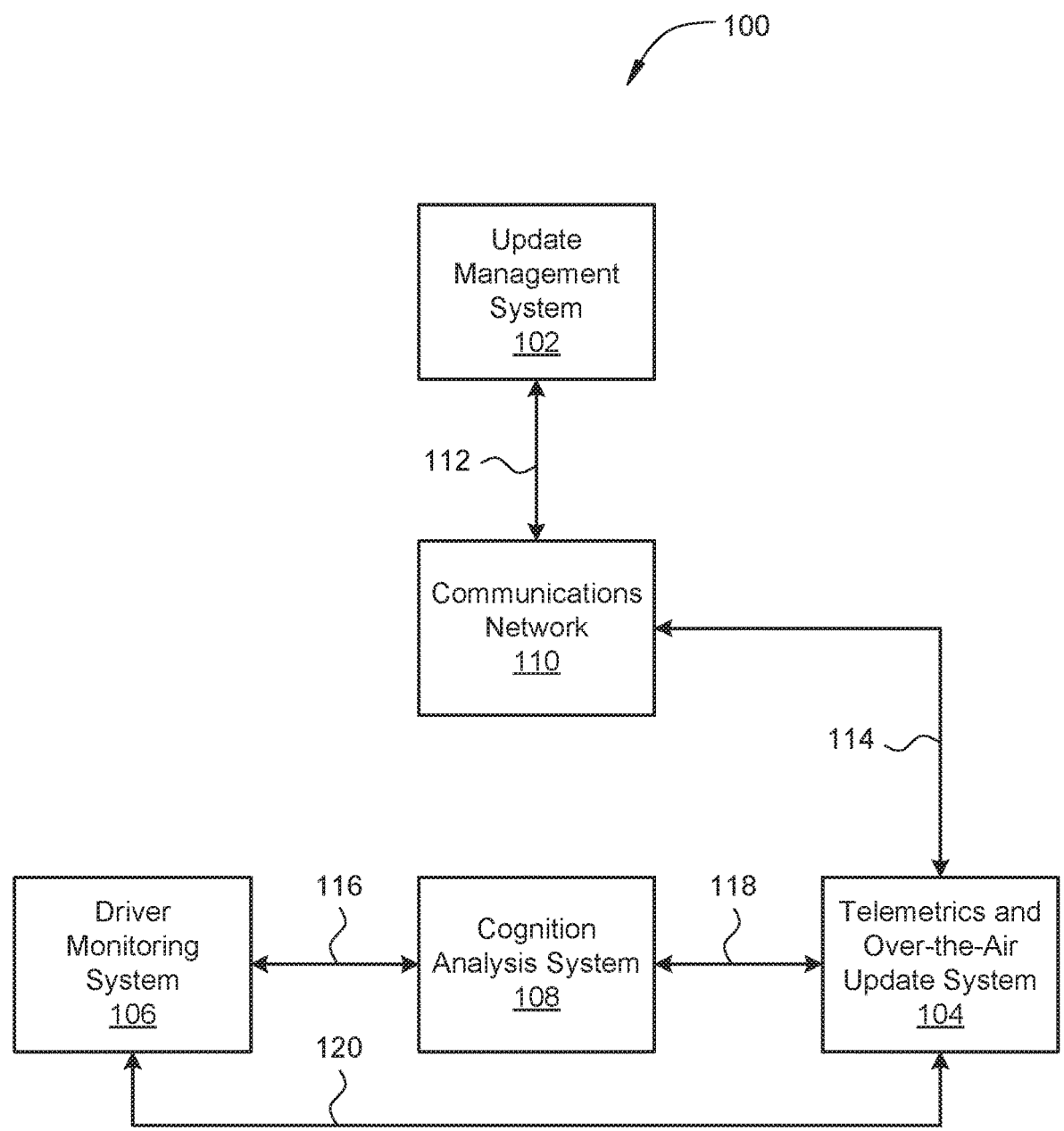
FIG. 1 illustrates a system configured to implement one or more aspects of the present disclosure.

FIG. 1 illustrates a system 100 configured to implement one or more aspects of the present disclosure. As shown, the system 100 includes, without limitation, an update management system 102, a telemetrics and over-the-air update system 104, a driver monitoring system 106, and a cognition analysis system 108. As used herein, "cognition" includes both cognitive workload and emotional state. The update management system 102 and telemetrics and over-the-air update system 104 are in communication with each other via a communications network 110. Communications network 110 may be any suitable environment to enable communications among remote or local computer systems and computing devices, including, without limitation, Bluetooth communications channels, wireless and wired LANs (Local Area Networks), and Internet-based WANs (Wide Area Networks). Update management system 102 and telemetrics and over-the-air update system 104 communicate over communications network 110 via communications links 112 and 114, respectively. Further, telemetrics and over-the-air update system 104 communicates with driver monitoring system 106 and cognition analysis system 108 via point-to-point communications links 120 and 118, respectively. Driver monitoring system 106 communicates with cognition analysis system 108 via point-to-point communications link 116. Communications links 116, 118, and 120 may employ any one or more technically feasible communications media and protocols, in any combination.

Update management system 102 includes, without limitation, a computing device that may be a standalone server, a cluster or "farm" of servers, one or more network appliances, or any other device suitable for implementing one or more aspects of the present disclosure. Illustratively, update management system 102 communicates over communications network 110 via communications link 112.

In operation, update management system 102 provides a mechanism for the software development team to generate, test, and release updates to software applications. When a new update to a software application is released, update management system 102 distributes the update to one or more systems that are configured to execute the update, including, without limitation, telemetrics and over-the-air update system 104, driver monitoring system 106, and cognition analysis system 108. As further described herein, the update may be distributed to the telemetrics and over-the-air update system 104, driver monitoring system 106, and cognition analysis system 108 via various techniques. These techniques, include, without limitation, installation via an over-the-air update process, retrieving and installing the update via a communications network, and installing the update via a physical medium. In some embodiments, update management system 102 may transmit the update via communications network 110 to telemetrics and over-the-air update system 104. Telemetrics and over-the-air update system 104 may receive the update and install the update on one or more of telemetrics and over-the-air update system 104, driver monitoring system 106, and cognition analysis system 108. In some embodiments, a user may retrieve the update from update management system 102 via communications network 110. In some embodiments, a user may retrieve the update from a physical medium, including, without limitation, a CD-ROM, a DVD, or a USB drive. After retrieving the update, the user may install the update on one or more of telemetrics and over-the-air update system 104, driver monitoring system 106, and cognition analysis system 108.

Further, update management system 102 receives cognitive reaction data from one or more cognition analysis system 108. Update management system 102 aggregates and analyzes the cognitive reaction data to determine whether the cognitive reaction of one or more users to each of the various modifications of an HMI included in the update indicates improved, unchanged, or diminished usability. The software development team may then review the aggregated and analyzed cognitive reaction data to determine whether each modification of the HMI should be retained, modified, or removed for subsequent updates.

Telemetrics and over-the-air update system 104 includes, without limitation, a computing device that may be a stand-alone server, a cluster or "farm" of servers, one or more network appliances, or any other device suitable for implementing one or more aspects of the present disclosure. Illustratively, telemetrics and over-the-air update system 104 communicates over communications network 110 via communications link 114. Further, telemetrics and over-the-air update system 104 communicates with driver monitoring system 106 and cognition analysis system 108 via point-to-point communications links 120 and 118, respectively.

In operation, telemetrics and over-the-air update system 104 receives measurement data from driver monitoring system 106 and/or cognition analysis system 108. The measurement data may include information related various components of system 100, including, without limitation, sensor data, instruments, camera images and video. The measurement data may further include processed data, where driver monitoring system 106 and/or cognition analysis system 108 analyzes certain measurement data, such as sensor data, instruments, camera images and video, and generates processed data therefrom. Such processed data may include, without limitation, cognitive workload data and emotional state data. Telemetrics and over-the-air update system 104 then transmits the measurement data from driver monitoring system 106 and/or cognition analysis system 108 to update management system 102 via communications network 110.

Further, when a new update to a software application is released, telemetrics and over-the-air update system 104 receives the update from update management system 102 via communications network 110. After receiving the update, telemetrics and over-the-air update system 104 installs the update on one or more of telemetrics and over-the-air update system 104, driver monitoring system 106, and cognition analysis system 108.

Driver monitoring system 106 includes, without limitation, a computing device that may be a standalone server, a cluster or "farm" of servers, one or more network appliances, or any other device suitable for implementing one or more aspects of the present disclosure. Illustratively, driver monitoring system 106 communicates with telemetrics and over-the-air update system 104 and cognition analysis system 108 via point-to-point communications links 120 and 116, respectively.

In operation, driver monitoring system 106 monitors a driver of a vehicle to determine certain characteristics, such as the alertness state of the driver. Driver monitoring system 106 receives measurement data via various devices, including, without limitation, cameras, microphones, infrared sensors, ultrasound sensors, radar sensors, thermal imaging sensors, heartrate and breathing monitors, and vehicle instrument sensors. By analyzing the measurement data, driver monitoring system 106 determines the overall physiological state of the driver, which may include alertness level of the driver. If driver monitoring system 106 determines that the driver is not sufficiently alert, driver monitoring system 106 may initiate certain responsive actions, including, without limitation, flashing an interior light, sounding an alarm, and applying brakes to slow or stop the vehicle safely. Further, driver monitoring system 106 transmits measurement data received via the various devices to cognition analysis system 108 for additional analysis, as further described herein.

Cognition analysis system 108 includes, without limitation, a computing device that may be a standalone server, a cluster or "farm" of servers, one or more network appliances, or any other device suitable for implementing one or more aspects of the present disclosure. Illustratively, cognition analysis system 108 communicates with telemetrics and over-the-air update system 104 and driver monitoring system 106 via point-to-point communications links 118 and 116, respectively.

In operation, cognition analysis system 108 receives measurement data from driver monitoring system 106. The measurement data is received via various devices associated with driver monitoring system 106. Cognition analysis system 108 analyzes the measurement data in order to generate processed data related to the cognitive workload and emotional state of the driver or other user, as further described herein. Cognition analysis system 108 stores one or both of the measurement data and the processed data in a data store. In some embodiments, cognition analysis system 108 may transmit the one or both of the measurement data and the processed data to telemetrics and over-the-air update system 104. Telemetrics and over-the-air update system 104 may then transmit the measurement data and/or processed data to update management system 102 via communications network 110.

It will be appreciated that the system shown herein is illustrative and that variations and modifications are possible. In one example, update management system 102, telemetrics and over-the-air update system 104, driver monitoring system 106, and cognition analysis system 108 are shown as communicating via certain networked and point-to-point communications links. However, update management system 102, telemetrics and over-the-air update system 104, driver monitoring system 106, and cognition analysis system 108 may communicate with each other via any technically feasible networked and point-to-point communications links in any technically feasible combination within the scope of this disclosure.

In another example, update management system 102, telemetrics and over-the-air update system 104, driver monitoring system 106, and cognition analysis system 108 are shown as separate systems included in the system 100 of FIG. 1. However, the techniques performed by update management system 102, telemetrics and over-the-air update system 104, driver monitoring system 106, and cognition analysis system 108 may be performed by one or more application programs executing on any technically feasible processor(s) included in one or more computing devices in any technically feasible combination. Such computing devices may include, without limitation, a head unit and an auxiliary unit deployed in a vehicle. In yet another example, update management system 102, telemetrics and over-the-air update system 104, driver monitoring system 106, and cognition analysis system 108 are shown and described in the context of a vehicle based computing system that receives updates to one or more software applications via an over-the-air update process to a vehicle-based system. However, the techniques described herein may be deployed in any technically feasible system that receives updates to software updates and can monitor cognitive workload and emotional state of a user, including, without limitation, a smartphone, a laptop computer, a tablet computer, and a deskside computer. In yet another example, system 100 may include any technically feasible number of update management systems 102, telemetrics and over-the-air update systems 104, driver monitoring systems 106, and cognition analysis systems 108, in any technically feasible combination.

Operations of the Cognition Analysis System

As further described herein, cognition analysis system 108 monitors and analyzes a user's cognitive reaction to an update to a software application. The update may be automatically installed via an OTA technique. Additionally or alternatively, a user may install the update after retrieving the update via a communications network or via a physical computer-readable medium. Cognition analysis system 108 monitors and analyzes cognitive workload and emotional state of the user when using a new or modified feature of a human-machine interface associated with the update. In so doing, cognition analysis system 108 assesses the cognitive reaction of the user in a contemporaneous and continuous manner.

Figure 2:
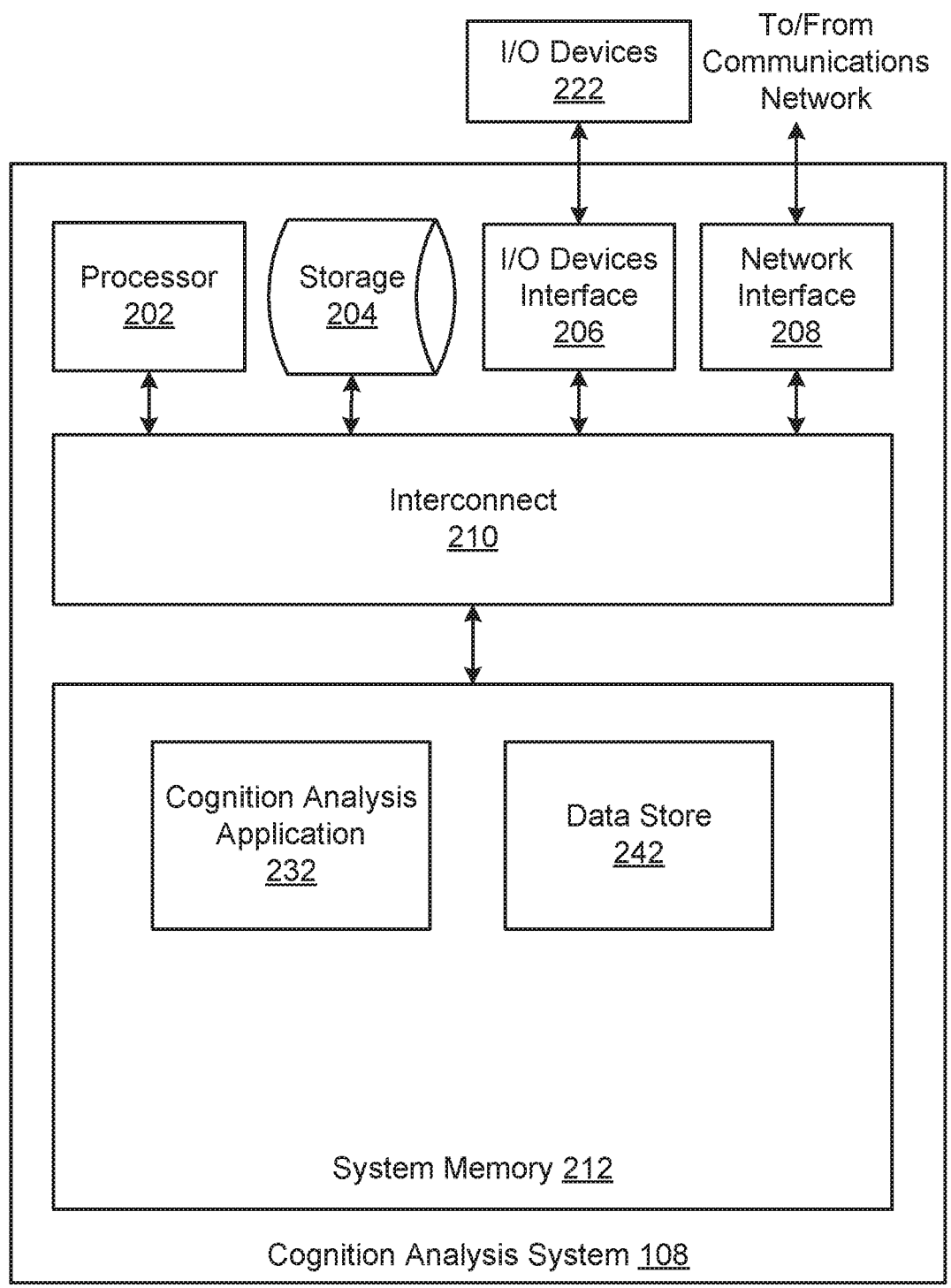
FIG. 2 is a more detailed illustration of the cognition analysis system of FIG. 1, according to various embodiments.

FIG. 2 is a more detailed illustration of the cognition analysis system 108 of FIG. 1, according to various embodiments. As shown, cognition analysis system 108 includes, without limitation, a processor 202, storage 204, an input/output (I/O) devices interface 206, a network interface 208, an interconnect 210, and a system memory 212.

The processor 202 retrieves and executes programming instructions stored in the system memory 212. Similarly, the processor 202 stores and retrieves application data residing in the system memory 212. The interconnect 210 facilitates transmission, such as of programming instructions and application data, between the processor 202, input/output (I/O) devices interface 206, storage 204, network interface 208, and system memory 212. The I/O devices interface 206 is configured to receive input data from user I/O devices 222. Examples of user I/O devices 222 may include one or more buttons, a keyboard, and a mouse or other pointing device. The I/O devices interface 206 may also include an audio output unit configured to generate an electrical audio output signal, and user I/O devices 222 may further include a speaker configured to generate an acoustic output in response to the electrical audio output signal. Another example of a user I/O device 222 is a display device that generally represents any technically feasible means for generating an image for display. For example, the display device could be a liquid crystal display (LCD) display, organic light-emitting diode (OLED) display, or digital light processing (DLP) display. The display device may be a TV that includes a broadcast or cable tuner for receiving digital or analog television signals. The display device may be included in a VR/AR headset or a heads-up display (HUD) assembly. Further, the display device may project an image onto one or more surfaces, such as walls, projection screens or a windshield of a vehicle. Additionally or alternatively, or may project an image directly onto the eyes of a user (e.g. via retinal projection).

Processor 202 is included to be representative of a single central processing unit (CPU), multiple CPUs, a single CPU having multiple processing cores, and the like. And the system memory 212 is generally included to be representative of a random access memory. The storage 204 may be a disk drive storage device. Although shown as a single unit, the storage 204 may be a combination of fixed and/or removable storage devices, such as fixed disc drives, floppy disc drives, tape drives, removable memory cards, or optical storage, network attached storage (NAS), or a storage area-network (SAN). Processor 202 communicates to other computing devices and systems via network interface 208, where network interface 208 is configured to transmit and receive data via a communications network.

The system memory 212 includes, without limitation, a cognition analysis application 232 and a data store 242. The cognition analysis application 232, when executed by the processor 202, performs one or more operations associated with the cognition analysis system 108 of FIG. 1, as further described herein. When performing the operations associated with the cognition analysis system 108, cognition analysis application 232 may store data in and retrieve data from data store 242.

In operation, cognition analysis application 232 receives a notification that a new update to a software application has been installed. The update may be automatically installed via an OTA technique. Additionally or alternatively, a user may install the update after retrieving the update via a communications network or via a physical computer-readable medium. The update includes one or modifications to the current software application. The modifications may include changes to, without limitation, an HMI associated with a display, a virtual instrument cluster, a heads-up display, or a voice interface. Cognition analysis application 232 detects that the user has interacted with a feature that is tagged for measurement. For example, the feature tagged for measurement could be associated with an HMI screen that includes a new graphical element or a graphical element that now has a different position, size, and/or color.

Upon detecting such a user interaction, cognition analysis application 232 begins acquiring sensor data related to the user's cognitive workload and emotional state. The sensor data is acquired along with timestamp data that correlates the sensor data with time. Cognition analysis application 232 analyzes the sensor data to generate processed data related to the cognitive workload and emotional state of the user. A change in cognitive workload and/or emotional state of the user that occurs after the user interacts with an HMI feature may relate to how the user reacts to the HMI feature. Cognition analysis application 232 then stores timestamped records of the sensor data and/or the processed data in data store 242. Cognition analysis application 232 transmits the timestamped records to telemetrics and over-the-air update system 104. Telemetrics and over-the-air update system 104 then transmits the timestamped records to update management system 102 via communications network 110 for further analysis. Additionally or alternatively, the user or another person may retrieve the timestamped records from data store 242 at a later time and manually transmit the timestamped records to update management system 102 for further analysis.

After receiving timestamped records from one or more cognition analysis systems 108, update management system 102 aggregates and analyzes the cognitive reaction data to measure whether various modifications of an HMI associated with the update show whether the cognitive reaction of one or more users to each modification indicates improved, unchanged, or diminished usability. The software development team may then review the aggregated and analyzed cognitive reaction data to determine whether each modification of the HMI should be retained, modified, or removed for subsequent updates.

Various types of sensor data and associated processing are now described in further detail. The sensor data is categorized as emotion sensing, physiology sensing, behavioral sensing, acoustic sensing, and pupillometry-based cognitive workload sensing.

Emotion sensing includes detecting and classifying emotions and emotional state. Emotional sensing includes detecting discreet and known emotions such as happiness, satisfaction, anger, and frustration. Emotional sensing includes computing parametrized metrics related to emotional state, such as emotional arousal level and emotional valence level. Emotional sensing is based on data received from various types of sensors.

Sensor data may be received from psychophysiological sensors that measure various biological and physiological signals associated with a user, including, without limitation, perspiration, heartrate, breathing rate, blood flow, blood oxygen levels, galvanic skin response, temperature, sounds uttered by a user, and behaviors of a user. Such sensor data represents various types of signals that are relevant for emotion detection. In addition, image data may be received from cameras and other imaging sensors that are configured to capture still and moving images, including, without limitation, color images, black and white images, thermal images, and infrared images. Such cameras and imaging sensors capture a user's facial expressions or other images of the user's body position or contortions that may be indicative of emotion. In some embodiments, images may be received from an array of cameras or imaging sensors in order to simultaneously capture multiple perspectives of the body and head of the user. Further, in some embodiments, images may be received from a depth camera or imaging sensor in order to sense body posture and body positioning.

Physiology sensing includes detection systems that capture various physiological signals that are correlated with emotional states. Signals received from such sensors correlate with certain emotional states, and, therefore, are relevant to emotion classification. For example, galvanic skin response may be indicative of the intensity of emotional state. Physiology sensors may include, without limitation, galvanic skin response sensors to measure change in the electrical resistance of the skin caused by emotional stress, imagers to detect blood oxygen levels, thermal sensors to detect blood flow, optical sensors to detect blood flow, EEG systems to detect surface potentials of the brain, EOG sensors (electrooculography sensors that measure eye movements by monitoring the electrical potential between the front and back of the human eye), EMG sensors (electromyography sensors that measure electrical activity in response to a nerve's stimulation of muscles), ECG sensors (electrocardiography sensors that measure the electrical activity of the heart), high-frequency radio sensors such as GHz band radios to measure heartrate and breathing rate, and neural systems to detect the neural correlates of emotion.

Acoustic sensing includes analyzing the words spoken by a user, as well as how a user speaks a given phrase, which are indicative of sentiment emotion. Acoustic sensing further includes non-speech human sounds emitted by a user, including, without limitation, whistling, humming, laughing, or screaming, which may be indicative of the user's emotional state. In one example, natural language processing methods, sentiment analysis, and speech analysis could measure emotion via the semantic meaning of language. In another example, voice tone analysis could detect emotion from the actual speech signal. Both methods could be used singly or in combination. Typical acoustic sensors data include, without limitation, a microphone, a microphone array, and other audio sensing technologies.

Behavioral sensing includes detecting a user's activities in and around the vehicle. Some of the sensors further described herein may be employed to detect movement in and around the vehicle. Application and service usage data may also indicate a user's behavior and infer emotion through a classification system. In one example, mobile usage data could indicate a pattern of application usage by the user that correlates with certain emotional states. If an application is categorized as a game application or a social application, executing such an application could be correlated with joy, happiness, and related social emotions. Behavioral sensors may further include, without limitation, cameras, imaging sensor, auditory sensors, depth cameras, and pressure sensors. These sensors register a user's body position, movements, and other behaviors in and around the vehicle. Such body position, movement, and behavior data could be correlated with emotions such as boredom, fatigue, and arousal. Behavioral sensors may further include, without limitation, touch sensors, acoustic sensors, and registrations of button presses or other user interface interactions that determine how a user is behaving in the vehicle. Such sensor data may indicate which systems a user is accessing and where the user is placing his or her hands at any given time.

Pupillometry-based cognitive workload sensing measure minute fluctuations in a user's pupil diameter. Such minute fluctuations have been scientifically linked to the cognitive workload a user is experiencing from moment to moment. Other related techniques may be employed to measure cognitive workload. Sensors that enable measurement of cognitive workload include, without limitation, cameras and imaging sensors that image a user's pupil and measure the change in pupil diameter. Such cameras and imaging sensors include, without limitation, infrared cameras, thermal sensors, high-resolution color or black and white cameras, and camera arrays that capture multiple perspectives of the body and head of the user. Physiological sensors include, without limitation, galvanic skin response sensors, heartrate sensors, and skin temperature sensors that measure cognitive workload at relatively low resolution. In some embodiments, EEG and other neural interfaces may detect multiple cognitive workload levels. Methods related to measuring cognitive workload from EEG and other neural data include spectral entropy, weighted mean frequency, bandwidth, and spectral edge frequency. In some embodiments, speech analysis may be employed for cognitive workload sensing. In particular, spectral centroid frequency and amplitude, with some parameter fitting for filter length and filter number may successfully classify various cognitive workload levels.

In some embodiments, cognition analysis application 232 may partition sensor data and processed data into several levels, where each level is associated with a different degree of abstraction. A first data level may include raw sensor data, including, without limitation, data from cameras, microphones, infrared sensors, and vehicle instrument sensors. A second data level may include biological data associated with the user, including, without limitation, heartrate, temperature, perspiration, head position, face position, pupil diameter data, and direction of eye gaze.

A third data level may include processed data that represents various higher states of the user, including, without limitation, cognitive workload and emotional state. The cognitive workload data represents the degree of mental activity experienced by user. The emotional state data indicates how the user feels. The emotional state data may be divided into emotional arousal data and emotional valence data. The emotional arousal data represents the degree of the emotional state experienced by user. The emotional valence data indicates whether the emotional state is associated with positive emotions, such as happiness and satisfaction, or with negative emotions, such as anger and frustration. A fourth data level may include processed data that represents attentiveness data and/or engagement data that represents whether the user is directing attention to and engaging with the HMI. Alternatively, the user may be directing attention to and engaging with something else, such as the instrument cluster, a passenger, or the environment external to the vehicle. The attentiveness data and engagement data may be employed to determine whether the cognitive workload data and emotional state data relates to the user's interaction with the HMI, or is due to some other factor.

In some embodiments, the sensor data and processed data may be employed to customize the HMI for an individual user. For example, an update may include a new arrangement, color, or shading of graphical elements for a particular HMI screen. The new arrangement, color, or shading of graphical elements may be associated with lower cognitive workload and a positive emotional experience for most users of the update with the new arrangement of graphical elements. However, cognition analysis application 232 may determine that a particular user experiences lower cognitive workload and a positive emotional experience for the previous version of the HMI screen relative to the updated HMI screen. As a result, cognition analysis application 232 may remove the updated HMI screen from the update for the particular user and revert to the previous version of the HMI screen. In this manner, cognition analysis application 232 may automatically customize the update for a particular user based on the cognitive workload data and emotional state data for that user.

In one particular example, a user enters his or her vehicle on a cold morning. Overnight, the cognition analysis application 232 has been updated by telemetrics and over-the-air update system 104 via communications network 110. The updated version of the cognition analysis application 232 includes new HMI screens with an altered layout of the lighting and fan user interface. Because the fan was blowing when the user parked the vehicle the previous evening, the fan unit begins blasting cold air through the vents of the vehicle. The user reaches over to the touchscreen to turn down the fan unit and notices that the design of the lighting and fan user interface has changed. The cognition analysis application 232 receives an indication that the user is initiating a user interaction with the newly updated HMI. For example, this indication may be received when the user begins interacting with a specific HMI screen that includes a modification. The cognition analysis application 232 may receive this indication from the HMI system. Additionally or alternatively, the cognition analysis application 232 may directly detect that the user is initiating a user interaction with the newly updated HMI. As a result of receiving an indication that the user is initiating a user interaction with the newly updated HMI, the cognition analysis application 232 begins to compute and analyze the cognitive workload and emotional state of the user, specifically in relation to the updated lighting and fan user interface.

The cognition analysis application 232 detects an increase in cognitive workload and emotional arousal level of the user, along with a negative emotional valence level. From this data, the cognition analysis application 232 determines that the user is experiencing a negative emotional reaction, such as anger, disgust, or frustration. The cognition analysis application 232 stores the cognitive workload and emotional state for subsequent retrieval and analysis. Additionally or alternatively, the cognition analysis application 232 transmits the cognitive workload and emotional state data to the telemetrics and over-the-air update system 104 via communications network 110. The telemetrics and over-the-air update system 104 transmits the cognitive workload and emotional state data to update management system 102 via communications network 110.

The user may tap the "fan" button and then the "off" button in order to turn off the fan unit. During the drive, the user may turn the fan unit back on and adjust the fan speed one or more times. Each time the user turns the fan unit on or off and/or changes the fan speed, the cognition analysis application 232 determines the cognitive workload and emotional state of the user. The cognition analysis application 232 continues to store the cognitive workload and emotional state data. Additionally or alternatively, the cognition analysis application 232 continues to transmit the cognitive workload and emotional state data to the telemetrics and over-the-air update system 104 via communications network 110. The telemetrics and over-the-air update system 104 continues to transmit the cognitive workload and emotional state data to update management system 102 via communications network 110.

Subsequently, update management system 102 performs an offline comparison of the user's cognitive workload and emotional state during these interactions with the new HMI included in the updated software application, relative to the user's cognitive workload and emotional state during interactions with the previous HMI. Via this offline comparison, update management system 102 may determine that the new HMI included in the updated software application has reduced the user's cognitive workload during interactions with the new HMI, thereby enabling a safer and easier interaction with the HMI. As a result, the software development team may leverage the analysis results generated by update management system 102 to determine whether the new HMI design is well-received by the user and whether the new HMI results in a lower cognitive workload and/or a positive emotional experience. The software development team may consider these analysis results when developing further HMI changes related to subsequent updates to the software application.

Figure 3A:
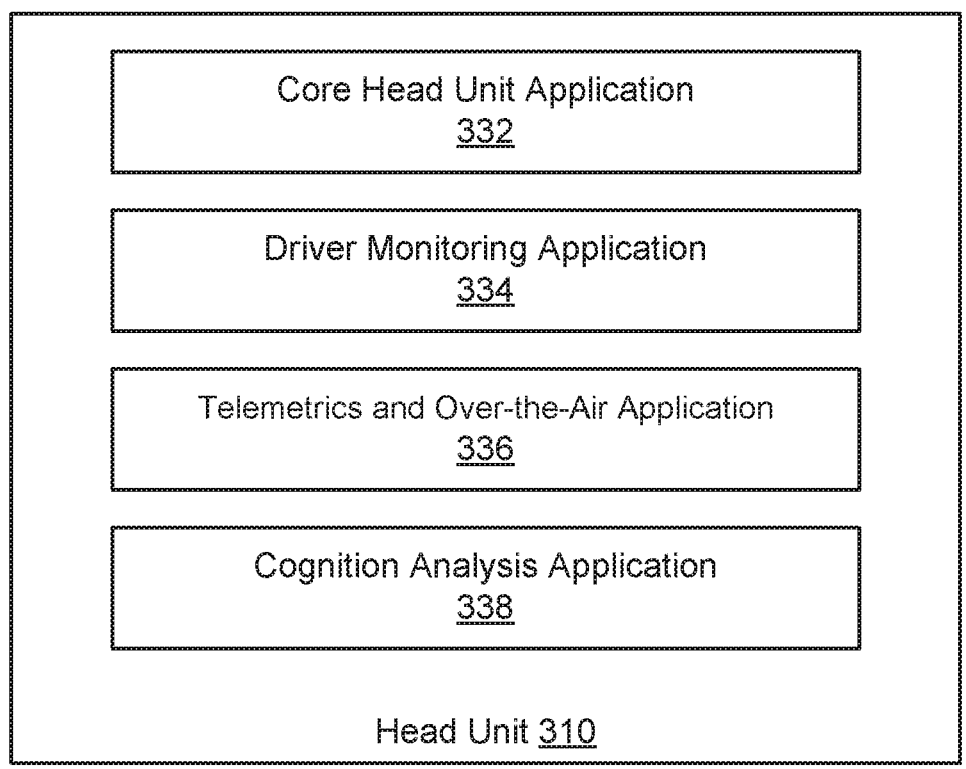
FIGS. 3A-3C are conceptual diagrams that illustrate various configurations of the system of FIG. 1, according to various embodiments.
Figure 3B:
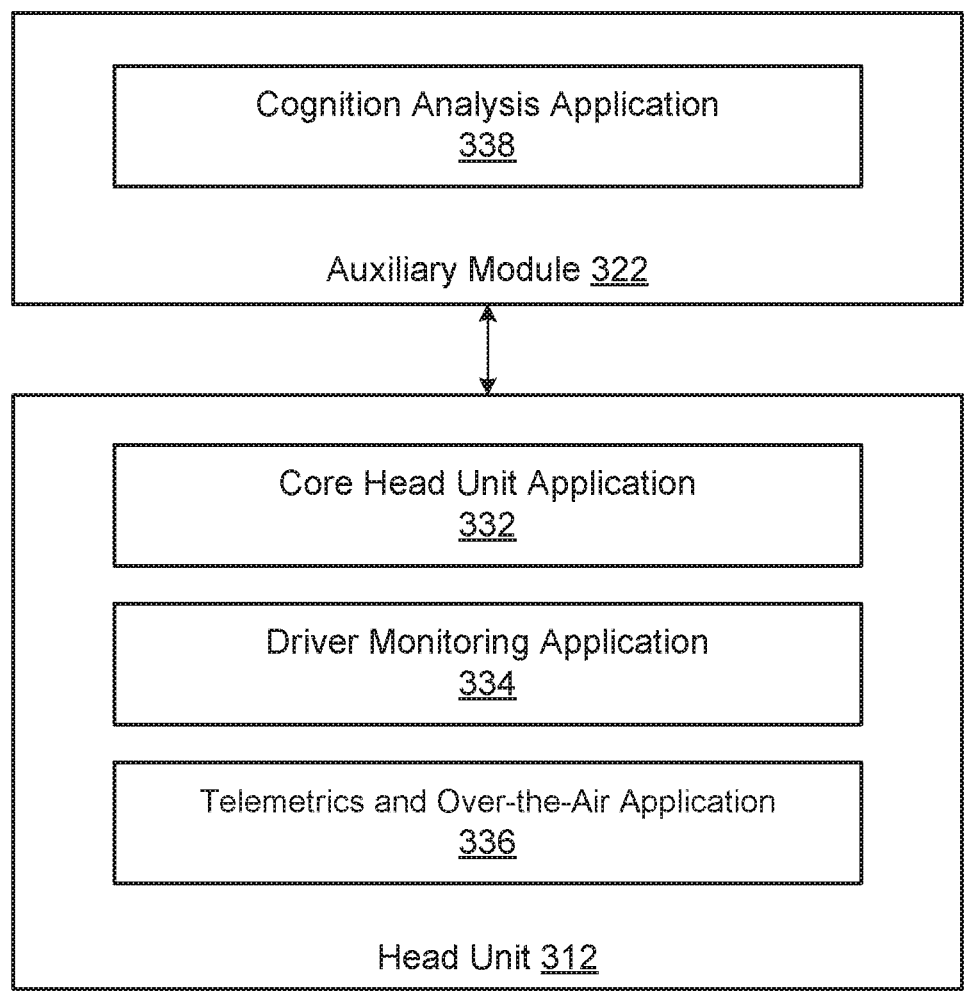
Figure 3C:
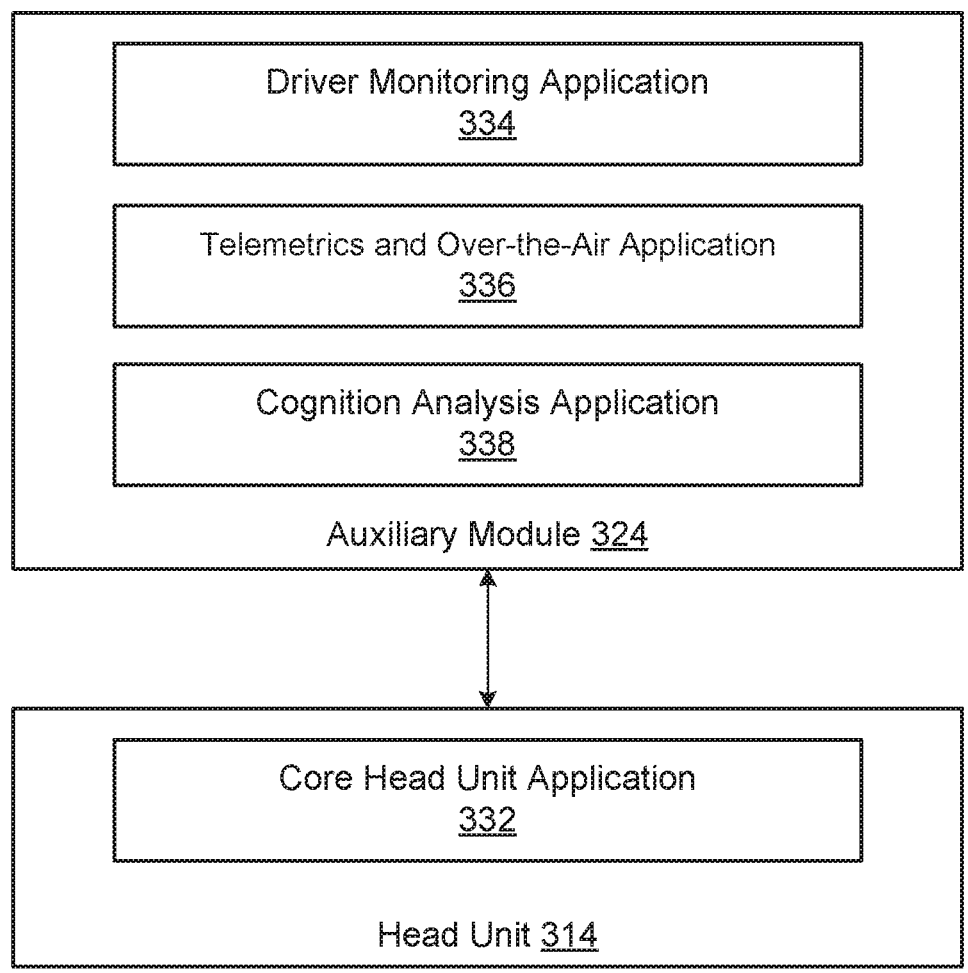

FIGS. 3A-3C are conceptual diagrams that illustrate various configurations of the system of FIG. 1, according to various embodiments.

As shown in FIG. 3A, a head unit 310 includes a core head unit application 332, a driver monitoring application 334, a telemetrics and over-the-air application 336, and a cognition analysis application 338. Head unit 310 includes a computing device with sufficient processing and memory resources associated with core head unit application 332, driver monitoring application 334, telemetrics and over-the-air application 336, and cognition analysis application 338. Core head unit application 332 performs various functions associated with the operation of a vehicle, including, without limitation, entertainment and media functions, navigation, and vehicle monitoring. Vehicle monitoring includes monitoring and display functions related to tire pressure, oil level, coolant temperature, vehicle maintenance and so on.

Driver monitoring application 334 performs various functions associated with the driver monitoring system 106 of FIG. 1. These functions include, without limitation, monitoring a driver of a vehicle to determine the alertness state of the driver, and transmitting measurement data received via various devices to cognition analysis application 338 for additional analysis.

Telemetrics and over-the-air application 336 performs various functions associated with the telemetrics and over-the-air system 104 of FIG. 1. These functions include, without limitation, receiving measurement data from driver monitoring system 106 and/or cognition analysis system 108, transmitting the measurement data to update management system 102, receiving updates of software applications from update management system 102 via communications network 110, and installing the updates.

Cognition analysis application 338 performs various functions associated with the cognition analysis system 108 of FIG. 1. These functions include, without limitation, receiving measurement data received via various devices from driver monitoring application 334, analyzing the measurement data in order to generate processed data related to the cognitive workload and emotional state of the driver or other user, and storing one or both of the measurement data and processed data. In some embodiments, cognition analysis application 338 may transmit the one or both of the measurement data and the processed data to telemetrics and over-the-air update application 336. Telemetrics and over-the-air update application 336 may then transmit the measurement data and/or processed data to update management system 102 via communications network 110.

In some embodiments, a head unit may not have sufficient processor and memory resources to execute all of head unit application 332, driver monitoring application 334, telemetrics and over-the-air application 336, and cognition analysis application 338. Consequently, one or more of these applications may be executed on a computing device associated with one or more auxiliary modules. Such auxiliary modules could include an internal computing device along with local and/or remote connectivity to one or more communications channels. One exemplary auxiliary module could be a "dongle" inserted into a port of a vehicle, such as an on-board diagnostics 2 (OBD2) port, where a dongle is a small device that may be connected to and in communication with another device, such as the head unit. Another exemplary auxiliary module could be a unit embedded into a dash panel of a vehicle or underneath a driver seat or passenger seat of the vehicle. Yet another exemplary auxiliary module could be a smartphone or other mobile device executing an application that communicates with another device, such as the head unit, over one or more wired or wireless communications channels. Any such auxiliary module may include a computing device that, when executing instructions, may perform any one or more techniques described herein. Further, any such auxiliary module may include may include a wired and/or wireless network interface to communicate with one or more local and/or remote devices.

As shown in FIG. 3B, a head unit 312 includes a core head unit application 332, a driver monitoring application 334, and a telemetrics and over-the-air application 336. Head unit 312 includes a computing device with sufficient processing and memory resources associated with core head unit application 332, driver monitoring application 334, and telemetrics and over-the-air application 336. Head unit 312 communicates with an auxiliary module 322 that includes a cognition analysis application 338. Auxiliary module 322 includes a computing device with sufficient processing and memory resources associated with cognition analysis application 338.

In some embodiments, a legacy head unit may only include the functions associated with core head unit application 332. In such embodiments, the remaining functions may be executed on a computing device associated with one or more auxiliary modules.

As shown in FIG. 3C, a head unit 314 includes a core head unit application 332. Head unit 312 includes a computing device with sufficient processing and memory resources associated with core head unit application 332. Head unit 312 communicates with an auxiliary module 322 that includes a driver monitoring application 334, and a telemetrics and over-the-air application 336, and a cognition analysis application 338. Auxiliary module 322 includes a computing device with sufficient processing and memory resources associated with driver monitoring application 334, and telemetrics and over-the-air application 336, cognition analysis application 338.

Although specific configurations are shown in FIGS. 3A-3C, the functions associated with core head unit application 332, driver monitoring application 334, telemetrics and over-the-air application 336, and cognition analysis application 338 may be executed on any one or more computing devices in any technically feasible combination and configuration within the scope of the present disclosure.

Figure 4A:
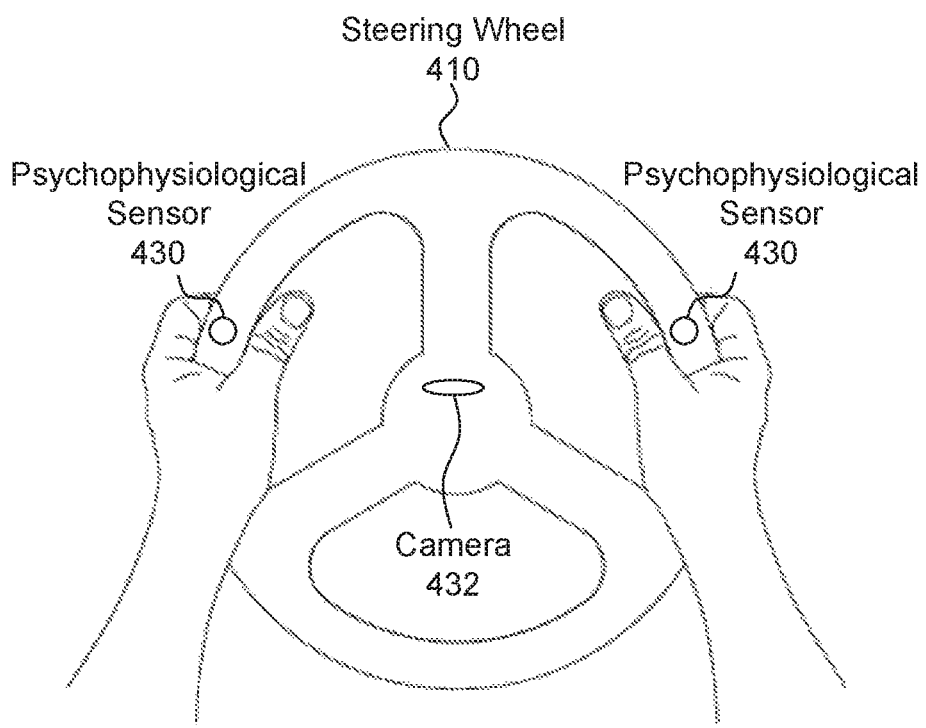
FIGS. 4A-4B illustrate example arrangements of sensors associated with the system of FIG. 1, according to various embodiments.
Figure 4B:
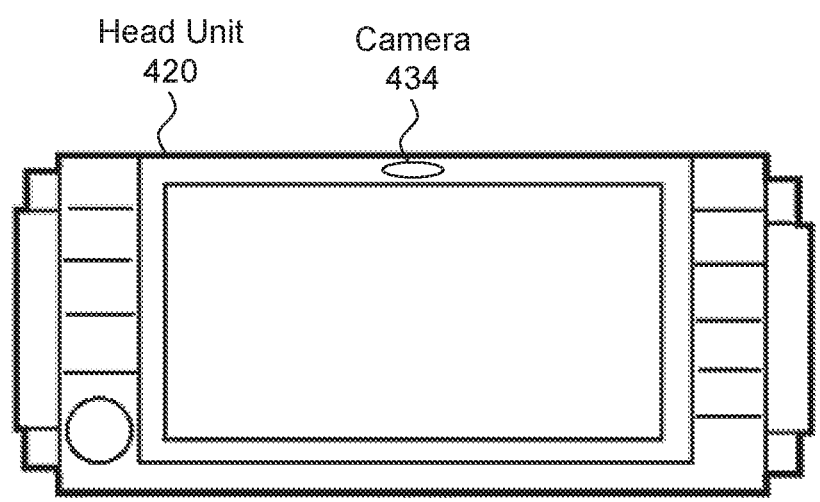

FIGS. 4A-4B illustrate example arrangements of sensors associated with the system of FIG. 1, according to various embodiments. As shown in FIG. 4A, a steering wheel 410 fitted with psychophysiological sensors 430 and a camera 432. The psychophysiological sensors 430 may be configured to measure any technically feasible psychophysiological data via contact with the hands of the user, including, without limitation, heartrate, temperature, and perspiration data. The camera 432 may capture still or moving images. The captured images may include any technically feasible image data, including, without limitation, color images, black and white images, thermal images, and infrared images. The psychophysiological sensors 430 and the camera 432 may transmit psychophysiological data and images to one or both of driver monitoring system 106 and cognition analysis system 108. As shown in FIG. 4B, a head unit 420 fitted with a camera 434. The camera 434 may capture still or moving images. The captured images may include any technically feasible image data, including, without limitation, color images, black and white images, thermal images, and infrared images. The camera 434 may transmit images to one or both of driver monitoring system 106 and cognition analysis system 108.

Figure 5A:
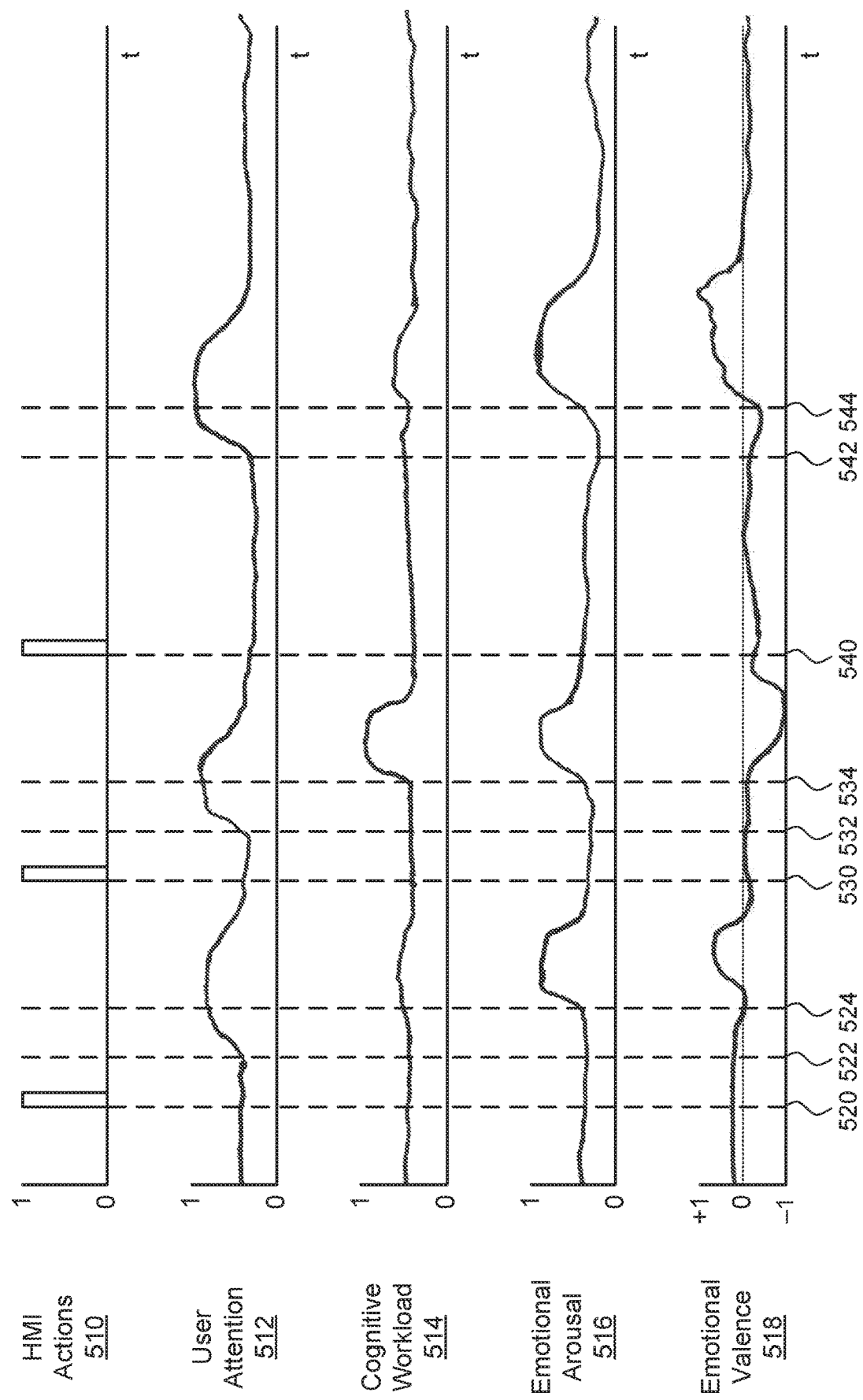

FIGS. 5A-5B illustrate example waveforms that illustrate cognitive workload and emotional state for a user associated with the system of FIG. 1, according to various embodiments. As shown, the waveforms include HMI actions 510, user attention 512, cognitive workload 514, emotional arousal 516, and emotional valence 518.

The HMI actions 510 waveform indicates when a feature that is tagged for measurement by cognition analysis system 108 is presented on a screen of the HMI. Typically, the value of the HMI actions 510 waveform remains at 0. When a feature tagged for measurement is presented on a screen of the HMI, the value of the HMI actions 510 waveform momentarily increases to 1 and then returns to 0.

The user attention 512 waveform indicates when the user pays attention to or engages with the feature that is tagged for measurement. The value of the user attention 512 waveform varies from 0, indicating a low attention level, to 1, indicating a high attention level.

The cognitive workload 514 waveform indicates the amount of mental effort exerted by the user. The value of the cognitive workload 514 waveform varies from 0, indicating a low cognitive workload level, to 1, indicating a high cognitive workload level.

The emotional arousal 516 waveform indicates the intensity of the emotional state experienced by the user. The value of the emotional arousal 516 waveform varies from 0, indicating a low emotional arousal level, to 1, indicating a high emotional arousal level.

The emotional valence 518 waveform indicates the direction of the emotional state experienced by the user. The value of the emotional valence 518 waveform varies from −1, indicating that the user is experiencing positive emotions, such as happiness and satisfaction, to +1, indicating that the user is experiencing negative emotions, such as anger and frustration. When the value of the emotional valence 518 waveform is zero, the user is experiencing neutral emotions that are neither positive emotions nor negative emotions.

As shown, four HMI actions 510 are illustrated in FIGS. 5A-5B, where the HMI actions 510 occur at time 520, 530, 540, and 550.

At time 520, cognition analysis system 108 detects that a first feature tagged for measurement is presented on a screen of the HMI, as evidenced by the value of the HMI actions 510 waveform momentarily increasing to 1 and then returning to 0. Beginning at time 522, cognition analysis system 108 detects that the value of the user attention 512 waveform is increasing. Based on this increase, cognition analysis system 108 may conclude that the user has seen the presentation of the first feature on the screen of the HMI and is engaging with the first feature. Beginning at time 524, cognition analysis system 108 detects that the value of the cognitive workload 514 waveform remains relatively stable. Based on this stable level, cognition analysis system 108 may conclude that the mental effort of the user is not increasing appreciably as a result of engaging with the first feature, indicating that the new feature was not difficult to understand and use. In addition, beginning at time 524, cognition analysis system 108 detects that the value of the emotional arousal 516 waveform is increasing and the value of the emotional valence 518 waveform is increasing from 0 to +1. Based on these value changes, cognition analysis system 108 may conclude that the user is experiencing positive emotions as a result of engaging with the first feature. By analyzing the cognitive workload 514, emotional arousal 516, and emotional valence 518 waveforms, cognition analysis system 108 may determine that the user has reacted positively to the first feature. After the passage of some time, cognition analysis system 108 then detects that the user attention 512, emotional arousal 516, and emotional valence 518 have returned to their respective quiescent levels. As a result, cognition analysis system 108 may conclude that the user is no longer engaging with the first feature.

At time 530, cognition analysis system 108 detects that a second feature tagged for measurement is presented on a screen of the HMI, as evidenced by the value of the HMI actions 510 waveform momentarily increasing to 1 and then returning to 0. Beginning at time 532, cognition analysis system 108 detects that the value of the user attention 512 waveform is increasing. Based on this increase, cognition analysis system 108 may conclude that the user has seen the presentation of the second feature on the screen of the HMI and is engaging with the second feature. Beginning at time 534, cognition analysis system 108 detects that the value of the cognitive workload 514 waveform is increasing. Based on this increase, cognition analysis system 108 may conclude that the mental effort of the user is increasing as a result of engaging with the second feature, indicating that the new feature was difficult to understand and use. In addition, beginning at time 534, cognition analysis system 108 detects that the value of the emotional arousal 516 waveform is increasing and the value of the emotional valence 518 waveform is decreasing from 0 to −1. Based on these value changes, cognition analysis system 108 may conclude that the user is experiencing negative emotions as a result of engaging with the second feature. By analyzing the cognitive workload 514, emotional arousal 516, and emotional valence 518 waveforms, cognition analysis system 108 may determine that the user has reacted negatively to the second feature. After the passage of some time, cognition analysis system 108 then detects that the user attention 512, cognitive workload 514, emotional arousal 516, and emotional valence 518 have returned to their respective quiescent levels. As a result, cognition analysis system 108 may conclude that the user is no longer engaging with the second feature.

At time 540, cognition analysis system 108 detects that a third feature tagged for measurement is presented on a screen of the HMI, as evidenced by the value of the HMI actions 510 waveform momentarily increasing to 1 and then returning to 0. Cognition analysis system 108 detects no changes in the user attention 512, cognitive workload 514, emotional arousal 516, and emotional valence 518 for a significant amount of time. Subsequently, at time 544, cognition analysis system 108 detects changes in the values of the user attention 512, cognitive workload 514, emotional arousal 516, and emotional valence 518 indicating an increase of the user's mental effort and a positive emotional reaction. Because of the significant delay between time 540 and time 544, cognition analysis system 108 may initially determine that the increase in mental effort and the positive emotional reaction is not due to the user's engagement with the third feature. However, cognition analysis system 108 also detects a significant delay between the presentation of the third feature at time 540 and an increase in the value of the user attention 512 waveform at time 542.

Cognition analysis system 108 further detects that the changes in the values of the user attention 512, cognitive workload 514, emotional arousal 516, and emotional valence 518 at time 544 occur soon after the increase in the value of the user attention 512 waveform at time 542. As a result, cognition analysis system 108 may determine that the user was distracted with other tasks for a period of time after the third feature was presented on the screen of the HMI. Therefore, cognition analysis system 108 may determine that the changes in the values of the user attention 512, cognitive workload 514, emotional arousal 516, and emotional valence 518 at time 544 are correlated to the presentation of the third feature at time 540. By analyzing the cognitive workload 514, emotional arousal 516, and emotional valence 518 waveforms, cognition analysis system 108 may determine that the user has reacted positively to the third feature. After the passage of some time, cognition analysis system 108 then detects that the user attention 512, cognitive workload 514, emotional arousal 516, and emotional valence 518 have returned to their respective quiescent levels. As a result, cognition analysis system 108 may conclude that the user is no longer engaging with the third feature.

At time 550, cognition analysis system 108 detects that a fourth feature tagged for measurement is presented on a screen of the HMI, as evidenced by the value of the HMI actions 510 waveform momentarily increasing to 1 and then returning to 0. Cognition analysis system 108 detects changes in the user attention 512, cognitive workload 514, emotional arousal 516, and emotional valence 518 at time 552, prior to the change in the HMI actions 510 waveform. Subsequently, at time 554, cognition analysis system 108 detects that the values of the user attention 512, cognitive workload 514, emotional arousal 516, and emotional valence 518 return to their prior levels. This pattern may be an indication that the user was attempting to understand the new fourth feature, such as figuring out where to press or looking for the feature on the new HMI screen. After looking at the new HMI screen and thinking about the new layout of the HMI screen for some time, the user presses the appropriate button on the HMI screen. The decrease in emotional valence 518 may indicate an initial negative reaction to the fourth feature. The subsequent increase in emotional valence 518 may indicate that the user eventually has a positive reaction to the fourth feature once the user understands the new HMI screen. In some embodiments, cognition analysis system 108 may store data related to user attention 512, cognitive workload 514, emotional arousal 516, and emotional valence 518 prior to an HMI action 510 over a rolling window of time in a data store. When a new HMI action 510 is detected, such as when a user presses a button, cognition analysis system 108 analyzes data in the rolling window data store to determine any changes in user attention 512, cognitive workload 514, emotional arousal 516, and emotional valence 518 that may have occurred prior to the HMI action 510.

It will be appreciated that the system shown herein is illustrative and that variations and modifications are possible. In one example, the HMI actions 510, user attention 512, cognitive workload 514, and emotional arousal 516 waveforms are shown as varying from a value of 0 to a value of 1. Similarly, the emotional valence 518 waveform is shown as varying from a value of −1 to a value of +1. However, the HMI actions 510, user attention 512, cognitive workload 514, emotional arousal 516, and emotional valence 518 waveforms may vary between any technically feasible values within the scope of the present disclosure.

In another example, cognition analysis system 108 could analyze data at multiple levels of granularity. At a first, coarse-granularity level, cognition analysis system 108 could analyze data to determine an overall reaction to a new update as a whole. At a second, medium-granularity level, cognition analysis system 108 could analyze data representing user reactions during various states, such as operating a navigation application, operating an audio streaming application, and executing certain combinations of states, applications, and use cases. With this second, medium-granularity level, cognition analysis system 108 could evaluate certain domains or general areas of functionality. In so doing, cognition analysis system 108 could sense the state of the navigation system, the infotainment system, and so on beyond individual user interactions with the HMI, such as button presses. At a third, fine-granularity level, cognition analysis system 108 could analyze data representing user reactions at the point of interaction with some function or button press on an HMI screen. FIGS. 5A-5B illustrate exemplary user reactions at this third, fine-granularity level.

Figure 6:
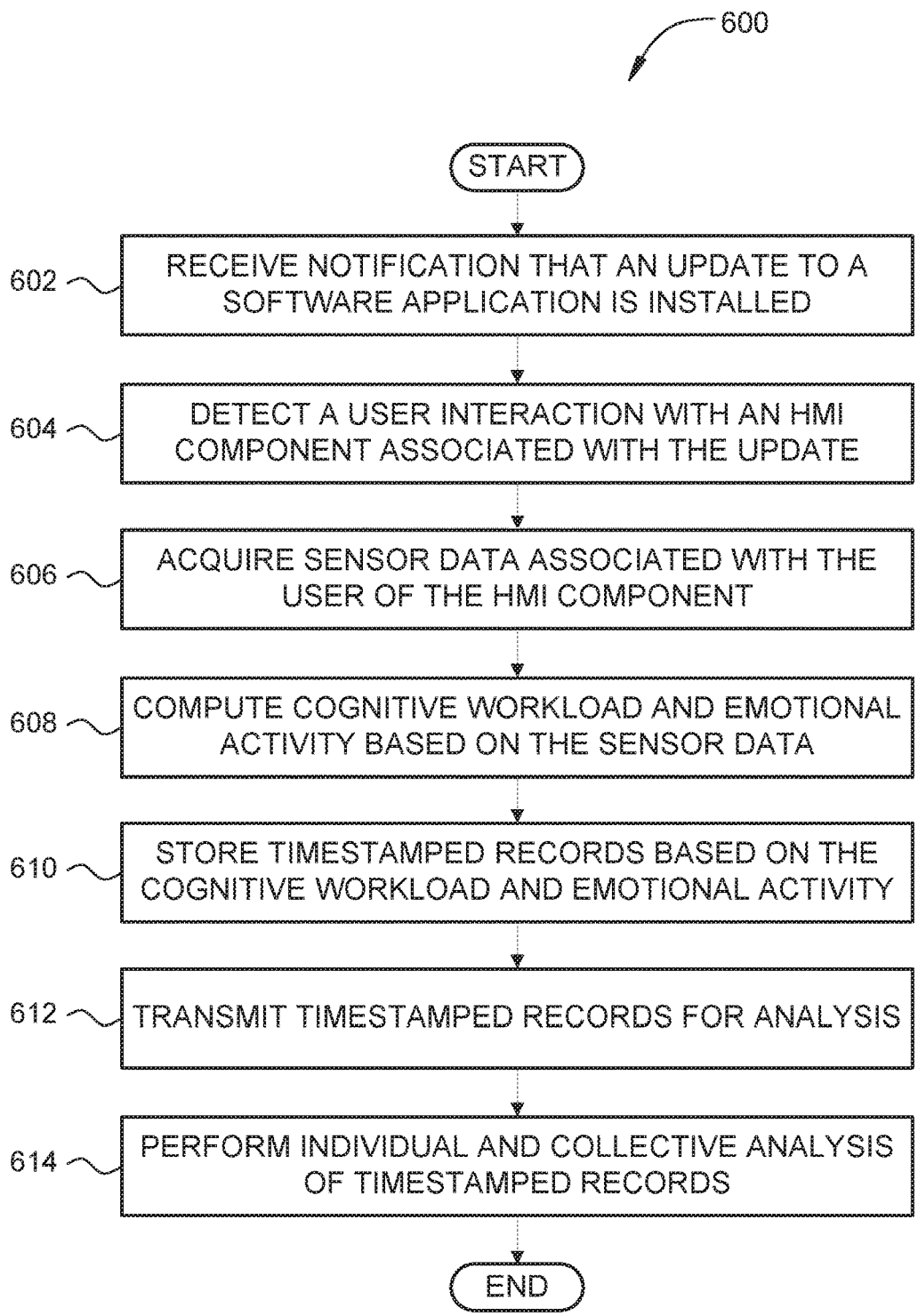
FIG. 6 is a flow diagram of method steps for computing and analyzing cognitive reaction to an update of a software application, according to various embodiments.

FIG. 6 is a flow diagram of method steps for computing and analyzing cognitive reaction to an update of a software application, according to various embodiments. Although the method steps are described in conjunction with the systems of FIGS. 1-5B, persons skilled in the art will understand that any system configured to perform the method steps, in any order, is within the scope of the present disclosure.

As shown, a method 600 begins at step 602, where a cognition analysis application 232 executing on a cognition analysis system 108 receives a notification that a new update to a software application has been installed. The update may be automatically installed via an OTA technique. Additionally or alternatively, a user may install the update after retrieving the update via a communications network or via a physical computer-readable medium. The update includes one or modifications to the current software application. The modifications may include changes to, without limitation, a human-machine interface associated with a display, a virtual instrument cluster, a heads-up display, or a voice interface. At step 604, cognition analysis application 232 detects that the user has interacted with a feature that is tagged for measurement. For example, the feature tagged for measurement could be associated with an HMI screen that includes a new graphical element or a graphical element that now has a different position, size, and/or color.

At step 606, upon detecting such a user interaction, cognition analysis application 232 begins acquiring sensor data related to the user's cognitive workload and emotional state. The sensor data is acquired along with timestamp data that correlates the sensor data with time. At step 608, cognition analysis application 232 analyzes the sensor data to compute and generate processed data related to the cognitive workload and emotional state of the user. A change in cognitive workload and/or emotional state of the user that occurs after the user interacts with an HMI feature may relate to how the user reacts to the HMI feature. At step 610, cognition analysis application 232 stores timestamped records of the sensor data and/or the processed data in data store 242. At step 612, cognition analysis application 232 transmits the timestamped records to telemetrics and over-the-air update system 104. Telemetrics and over-the-air update system 104 then transmits the timestamped records to update management system 102 via communications network 110 for further analysis. Additionally or alternatively, the user or another person may retrieve the timestamped records from data store 242 at a later time and manually transmit the timestamped records to update management system 102 for further analysis.

At step 614, after receiving timestamped records from one or more cognition analysis systems 108, update management system 102 performs individual and collective analysis of the timestamped records. In particular, update management system 102 aggregates and analyzes the cognitive reaction data to determine whether the cognitive reaction of one or more users to each of the various modifications of an HMI included in the update indicates improved, unchanged, or diminished usability. The software development team may then review the aggregated and analyzed cognitive reaction data to determine whether each modification of the HMI should be retained, modified, or removed for subsequent updates. The method then terminates.

In sum, a cognition analysis system assesses cognitive reaction to updates associated with a software application. The cognition analysis system measures the cognitive and emotional state of a user in order to obtain a quantitative assessment of the reactions and opinions of users with respect to updates to a human-machine interface (HMI) associated with a software application. For example, a driver monitoring system (DMS) could receive an over-the-air (OTA) update to the DMS software application and install the update. The cognition analysis system assesses the user's reactions while using the new HMI for the first time. The cognition analysis system performs the assessment via one or more sensors such as a camera, microphone, infrared sensor, ultrasound sensor, radar sensor, thermal imaging sensor, heartrate monitor, and breathing monitor. Based on data received from these sensors, the cognition analysis system can determine the user's cognitive workload and emotional state based on various aspects of the user, such as eye gaze, head position, face position, heartrate, and so on. The cognition analysis system correlates the cognitive workload and emotional state with activities related to the HMI, such as displaying a new screen via the HMI and detecting the activation of a control vial the HMI. As a result, the cognition analysis system assesses the user's reactions while using a new HMI for the first time. Via the cognition analysis system, the user's reactions to updates to the HMI are quantitatively measured when released to users. Data gathered and/or generated by the cognition analysis system is sent to the software development team in order to analyze the HMI changes that were deployed. The data is then employed by the software development team to make further changes to subsequent updates of the software application.

At least one technical advantage of the disclosed techniques relative to the prior art is that data associated with a user reaction to a software application update is acquired and analyzed after the update is released to users. As a result, user reaction to a new update may be continually assessed in the user environment after the update is released. Another technical advantage of the disclosed techniques is that, because the user reaction data is based on visual and/or psychophysiological information related to the user, the user reaction data is more accurate and less subject to bias relative to prior approaches, such as approaches involving user surveys and forum posts. As a result, a software development team is able to improve aspects of a software application based on a more accurate model of user reaction to a particular release of the software application. These technical advantages represent one or more technological improvements over prior art approaches.

1. In some embodiments, a computer-implemented method for determining a cognitive reaction to a software application update comprises: determining that a software application executing on a computing device has been modified into an updated software application; acquiring, via at least one sensor, sensor data associated with a user of the updated software application; and determining, based on the sensor data, at least one of a cognitive workload and an emotional state associated with a user interaction with a feature of the updated software application.

2. The computer-implemented method according to clause 1, wherein determining that the software application executing on the computing device has been updated comprises determining that an over-the-air update associated with the software application has been installed on the computing device.

3. The computer-implemented method according to clause 1 or clause 2, wherein the sensor data includes at least one image of the user of the software application, and wherein determining the at least one of the cognitive workload and the emotional state comprises analyzing the at least one image of the user of the software application.

4. The computer-implemented method according to any of clauses 1-3, wherein the sensor data includes at least one of a heartrate, a breathing rate, and a galvanic skin response of the user, and wherein determining the at least one of the cognitive workload and the emotional state comprises analyzing the at least one of the heartrate, the breathing rate, and the galvanic skin response of the user.

5. The computer-implemented method according to any of clauses 1-4, further comprising: detecting that a human-machine interface is displaying a graphical element associated with the feature; and correlating the at least one of the cognitive workload and the emotional state with a time that the graphical element was displayed.

6. The computer-implemented method according to any of clauses 1-5, further comprising: detecting that a human-machine interface is displaying a graphical element associated with the feature; detecting that the user has interacted with the graphical element; and correlating a time that the graphical element was displayed with a time at which the user interacted with the graphical element.

7. The computer-implemented method according to any of clauses 1-6, storing the at least one of the cognitive workload and the emotional state in a memory for subsequent retrieval and analysis.

8. The computer-implemented method according to any of clauses 1-7, causing the at least one of the cognitive workload and the emotional state to be transmitted via a telemetrics system via a communications network.

9. The computer-implemented method according to any of clauses 1-8, wherein the emotional state comprises an emotional arousal level and an emotional valence level.

10. In some embodiments, a computer-readable storage medium includes instructions that, when executed by a processor, cause the processor to determine a cognitive reaction to a software application update, by performing the steps of: determining that a software application executing on a computing device has been modified into an updated software application; acquiring, via at least one sensor, sensor data associated with a user of the updated software application; and determining, based on the sensor data, at least one of a cognitive workload, an emotional arousal level, and an emotional valence level associated with a user interaction with a feature of the updated software application.

11. The computer-readable storage medium according to clause 10, wherein determining that the software application executing on the computing device has been updated comprises determining that an over-the-air update associated with the software application has been installed on the computing device.

12. The computer-readable storage medium according to clause 10 or clause 11, wherein the sensor data includes at least one image of the user of the software application, and wherein determining the at least one of the cognitive workload, the emotional arousal level, and the emotional valence level comprises analyzing the at least one image of the user of the software application.

13. The computer-readable storage medium according to any of clauses 10-12, wherein the sensor data includes at least one of a heartrate, a breathing rate, and a galvanic skin response of the user, and wherein determining the at least one of the cognitive workload, the emotional arousal level, and the emotional valence level comprises analyzing the at least one of the heartrate, the breathing rate, and the galvanic skin response of the user.

14. The computer-readable storage medium according to any of clauses 10-according to any of clauses 10-13, further comprising: detecting that a human-machine interface is displaying a graphical element associated with the feature; and correlating the at least one of the cognitive workload, the emotional arousal level, and the emotional valence level with a time that the graphical element was displayed.

15. The computer-readable storage medium according to any of clauses 10-14, further comprising: detecting that a human-machine interface is displaying a graphical element associated with the feature; detecting that the user has interacted with the graphical element; and correlating a time that the graphical element was displayed with a time at which the user interacted with the graphical element.

16. The computer-readable storage medium according to any of clauses 10-15, storing the at least one of the cognitive workload, the emotional arousal level, and the emotional valence level in a memory for subsequent retrieval and analysis.

17. The computer-readable storage medium according to any of clauses 10-16, further comprising: detecting that a human-machine interface is displaying a graphical element associated with the feature; correlating the emotional valence level with a time that the graphical element was displayed; detecting that the emotional valence level is associated with a positive emotional state; and in response, retaining the feature of the updated software application.

18. The computer-readable storage medium according to any of clauses 10-17, further comprising: detecting that a human-machine interface is displaying a graphical element associated with the feature; correlating the emotional valence level with a time that the graphical element was displayed; detecting that the emotional valence level is associated with a negative emotional state; and in response, replacing the feature of the updated software application with a previous version of the feature.

19. In some embodiments, a system, comprises: a driver monitoring system; and a cognition analysis system coupled to the driver monitoring system and configured to: determining that a software application executing on a computing device has been modified into an updated software application; acquiring, via at least one sensor include in the driver analysis system, sensor data associated with a user of the updated software application; and determining, based on the sensor data, at least one of a cognitive workload and an emotional state associated with a user interaction with a feature of the updated software application.

20. The system according to clause 19, wherein determining that the software application executing on the computing device has been updated comprises determining that an over-the-air update associated with the software application has been installed on the computing device.

Any and all combinations of any of the claim elements recited in any of the claims and/or any elements described in this application, in any fashion, fall within the contemplated scope of the present disclosure and protection.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, enable the implementation of the functions/acts specified in the flowchart and/or block diagram block or blocks. Such processors may be, without limitation, general purpose processors, special-purpose processors, application-specific processors, or field-programmable The flowchart and block diagrams in the figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the preceding is directed to embodiments of the present disclosure, other and further embodiments of the disclosure may be devised without departing from the basic scope thereof, and the scope thereof is determined by the claims that follow.

What is claimed is:

1. A computer-implemented method for determining a cognitive reaction to a software application update, the method comprising:
    determining that a software application update is received for a software application executing on a computing device and results in an updated software application;
    in response to determining that the software application update has been received, acquiring, via at least one sensor, sensor data associated with a user of the updated software application;
    determining, based on the sensor data, at least one of a cognitive workload or an emotional state associated with a user interaction with a feature of the updated software application over a rolling window of time; and
    analyzing data over the rolling window of time to determine a change in the at least one of the cognitive workload or the emotional state that occurred after the feature is presented and prior to the user interaction.

2. The computer-implemented method of claim 1, wherein determining that the software application update has been received comprises determining that an over-the-air update associated with the software application has been installed on the computing device.

3. The computer-implemented method of claim 1, wherein the sensor data includes at least one image of the user of the software application, and wherein determining the at least one of the cognitive workload or the emotional state comprises analyzing the at least one image of the user of the software application.

4. The computer-implemented method of claim 1, wherein the sensor data includes at least one of a heartrate, a breathing rate, or a galvanic skin response of the user, and wherein determining the at least one of the cognitive workload or the emotional state comprises analyzing the at least one of the heartrate, the breathing rate, or the galvanic skin response of the user.

5. The computer-implemented method of claim 1, further comprising:
    detecting that a human-machine interface is displaying a graphical element associated with the feature; and
    correlating the at least one of the cognitive workload or the emotional state with a time that the graphical element was displayed.

6. The computer-implemented method of claim 1, further comprising:
    detecting that a human-machine interface is displaying a graphical element associated with the feature;
    detecting that the user has interacted with the graphical element; and correlating a time that the graphical element was displayed with a time at which the user interacted with the graphical element.

7. The computer-implemented method of claim 1, further comprising causing the at least one of the cognitive workload or the emotional state to be transmitted via a telemetrics system via a communications network.

8. The computer-implemented method of claim 1, wherein the emotional state comprises an emotional arousal level and an emotional valence level.

9. The computer-implemented method of claim 1, further comprising determining that the user has interacted with one or more features included in the updated software application that are tagged for measurement, wherein acquiring the sensor data occurs in response to determining that the user has interacted with the one or more features.

10. One or more non-transitory computer-readable storage media including instructions that, when executed by one or more processors, cause the one or more processors to determine a cognitive reaction to a software application update, by performing the steps of:
    determining that a software application update is received for a software application executing on a computing device and results in an updated software application;
    in response to determining that the software application update has been received, acquiring, via at least one sensor, sensor data associated with a user of the updated software application;
    determining, based on the sensor data, at least one of a cognitive workload, an emotional arousal level, or an emotional valence level associated with a user interaction with a feature of the updated software application over a rolling window of time; and
    analyzing data over the rolling window of time to determine a change in the at least one of the cognitive workload, the emotional arousal level, or the emotional valence level that occurred after the feature is presented and prior to the user interaction.

11. The one or more non-transitory computer-readable storage media of claim 10, wherein determining that the software application update has been received comprises determining that an over-the-air update associated with the software application has been installed on the computing device.

12. The one or more non-transitory computer-readable storage media of claim 10, wherein the sensor data includes at least one image of the user of the software application, and wherein determining the at least one of the cognitive workload, the emotional arousal level, or the emotional valence level comprises analyzing the at least one image of the user of the software application.

13. The one or more non-transitory computer-readable storage media of claim 10, wherein the sensor data includes at least one of a heartrate, a breathing rate, or a galvanic skin response of the user, and wherein determining the at least one of the cognitive workload, the emotional arousal level, or the emotional valence level comprises analyzing the at least one of the heartrate, the breathing rate, or the galvanic skin response of the user.

14. The one or more non-transitory computer-readable storage media of claim 10, further comprising:
    detecting that a human-machine interface is displaying a graphical element associated with the feature; and
    correlating the at least one of the cognitive workload, the emotional arousal level, or the emotional valence level with a time that the graphical element was displayed.

15. The one or more non-transitory computer-readable storage media of claim 10, wherein the steps further comprise:
    detecting that a human-machine interface is displaying a graphical element associated with the feature;
    detecting that the user has interacted with the graphical element; and
    correlating a time that the graphical element was displayed with a time at which the user interacted with the graphical element.

16. The one or more non-transitory computer-readable storage media of claim 10, wherein the steps further comprise storing the at least one of the cognitive workload, the emotional arousal level, or the emotional valence level in a memory for subsequent retrieval and analysis.

17. The one or more non-transitory computer-readable storage media of claim 10, wherein the steps further comprise:
    detecting that a human-machine interface is displaying a graphical element associated with the feature;
    correlating the emotional valence level with a time that the graphical element was displayed;
    detecting that the emotional valence level is associated with a positive emotional state; and
    in response, retaining the feature of the updated software application.

18. The one or more non-transitory computer-readable storage media of claim 10, wherein the steps further comprise:
    detecting that a human-machine interface is displaying a graphical element associated with the feature;
    correlating the emotional valence level with a time that the graphical element was displayed;
    detecting that the emotional valence level is associated with a negative emotional state; and
    in response, replacing the feature of the updated software application with a previous version of the feature.

19. A system, comprising:
    a driver monitoring system; and
    a cognition analysis system coupled to the driver monitoring system and configured to perform the steps of:
        determining that a software application update is received for a software application executing on a computing device and results in an updated software application;
        in response to determining that the software application update has been received, acquiring, via at least one sensor, sensor data associated with a user of the updated software application;
        determining, based on the sensor data, at least one of a cognitive workload or an emotional state associated with a user interaction with a feature of the updated software application over a rolling window of time; and
        analyzing data over the rolling window of time to determine a change in the at least one of the cognitive workload or the emotional state that occurred after the feature is presented and prior to the user interaction.

20. The system of claim 19, wherein determining that the software application update has been received comprises determining that an over-the-air update associated with the software application has been installed on the computing device.

* * * * *